(12) United States Patent
Merkle

(10) Patent No.: US 8,158,961 B2
(45) Date of Patent: Apr. 17, 2012

(54) OPHTHALMIC LENS CASE EQUIPPED WITH AN ULTRAVIOLET LIGHT SOURCE

(75) Inventor: Denise Lynn Merkle, Ft. Worth, TX (US)

(73) Assignee: SciConsult, Inc., Ft. Worth, TX (US)

( * ) Notice: Subject to any disclaimer, the term of this patent is extended or adjusted under 35 U.S.C. 154(b) by 110 days.

(21) Appl. No.: 12/848,033

(22) Filed: Jul. 30, 2010

(65) Prior Publication Data
US 2011/0024649 A1 Feb. 3, 2011

Related U.S. Application Data

(60) Provisional application No. 61/230,219, filed on Jul. 31, 2009.

(51) Int. Cl.
*B29D 11/00* (2006.01)
*G02C 7/02* (2006.01)
*G01N 21/33* (2006.01)

(52) U.S. Cl. .............. 250/504 R; 250/365; 264/1.38; 264/1.36; 351/159; 425/174.4

(58) Field of Classification Search .............. 250/504 R, 250/365; 264/1.38, 1.36; 351/159; 425/174.4
See application file for complete search history.

(56) References Cited

U.S. PATENT DOCUMENTS

| | | |
|---|---|---|
| 1,988,169 A | 1/1935 | Duckwall |
| 3,029,694 A | 4/1962 | Dantzic |
| 3,080,964 A | 3/1963 | Robinson et al. |
| 3,695,280 A | 10/1972 | Sturgeon |
| 3,770,113 A | 11/1973 | Thomas |
| 3,791,689 A | 2/1974 | Boone et al. |
| 3,822,096 A | 7/1974 | Wilms et al. |
| 3,917,391 A | 11/1975 | Padula et al. |
| 3,977,517 A | 8/1976 | Kadlecik et al. |
| 3,981,593 A | 9/1976 | Boyle |
| 4,173,281 A | 11/1979 | Trought |
| 4,235,842 A | 11/1980 | Thomas et al. |
| 4,251,719 A | 2/1981 | Ryder |
| 4,269,307 A | 5/1981 | LaHaye |
| 4,415,076 A | 11/1983 | Campbell |
| 4,508,216 A | 4/1985 | Kelman |
| 4,545,479 A | 10/1985 | Figari |
| 4,623,249 A | 11/1986 | Grant |
| 4,691,820 A | 9/1987 | Martinez |

(Continued)

FOREIGN PATENT DOCUMENTS
GB 2 093 605 9/1982

OTHER PUBLICATIONS

Garrett, Q. et al.; Hydrogel Lens Monomer Constituents Modulate Protein Sorption; Investigative Ophthalmology & Visual Science; Jun. 2000, vol. 41, No. 7; pp. 1687-1695.

(Continued)

*Primary Examiner* — Nikita Wells
(74) *Attorney, Agent, or Firm* — John A. Fortkort; Fortkort & Houston P.C.

(57) ABSTRACT

A container (101) for contact lenses is provided which comprises a chamber (105) adapted to store an ophthalmic lens in a fluid medium, a window for viewing a lens disposed in the chamber, and a UV light source adapted to illuminate the lens with UV radiation.

16 Claims, 2 Drawing Sheets

U.S. PATENT DOCUMENTS

| | | | |
|---|---|---|---|
| 4,710,023 A | 12/1987 | Loveridge | |
| 4,784,258 A | 11/1988 | Figari | |
| 4,865,186 A | 9/1989 | Gates | |
| 4,951,064 A | 8/1990 | Kun et al. | |
| 4,981,657 A | 1/1991 | Ryder | |
| 5,042,655 A | 8/1991 | Beldyk et al. | |
| 5,086,913 A | 2/1992 | Camm et al. | |
| 5,099,987 A | 3/1992 | Bieri | |
| 5,173,738 A | 12/1992 | Bieri | |
| 5,337,888 A | 8/1994 | Morrison | |
| 5,440,458 A | 8/1995 | Volk | |
| 6,086,799 A * | 7/2000 | Buazza et al. | 264/1.38 |
| 6,092,646 A | 7/2000 | Glazier | |
| 6,134,342 A | 10/2000 | Doke et al. | |
| 6,143,244 A | 11/2000 | Xia et al. | |
| 6,174,465 B1 * | 1/2001 | Buazza et al. | 264/1.38 |
| 6,259,518 B1 * | 7/2001 | Russell et al. | 356/124 |
| 6,286,520 B1 | 9/2001 | Lin | |
| 6,301,005 B1 | 10/2001 | Epstein et al. | |
| 6,309,658 B1 | 10/2001 | Xia et al. | |
| 6,491,281 B1 * | 12/2002 | Gotou et al. | 249/114.1 |
| 6,765,661 B2 | 7/2004 | Biel et al. | |
| D496,790 S | 10/2004 | Dzwill et al. | |
| 7,901,075 B2 * | 3/2011 | Rooney et al. | 351/177 |
| 2004/0158323 A1 | 8/2004 | Lisk, Jr. et al. | |
| 2006/0197067 A1 | 9/2006 | Xia et al. | |

OTHER PUBLICATIONS

Mok, Kwok Hei et al.; Effectiveness of No-Rub Contact Lens Cleaning on Protein Removal: A Pilot Study; Optometry and Vision Science; vol. 81, No. 6, Jun. 2004; pp. 468-470.

* cited by examiner

OPHTHALMIC LENS CASE EQUIPPED WITH AN ULTRAVIOLET LIGHT SOURCE

This application claims the benefit of priority from U.S. Provisional Application No. 61/230,219 filed Jul. 31, 2009, having the same title, and having the same inventor, and which is incorporated herein by reference in its entirety.

FIELD OF THE DISCLOSURE

The present disclosure relates generally to ophthalmic lenses, and more particularly, to a container for contact lenses which is equipped with an ultraviolet light source.

BACKGROUND OF THE DISCLOSURE

Contact lenses trace their history as far back as 1508, when Leonardo da Vinci described in his writings a method of directly altering corneal power by submerging the eye in a bowl of water. René Descartes proposed a related idea in 1636 which involved the placement of a glass tube filled with liquid in direct contact with the cornea. The first wearable contact lenses were created by German physiologist Adolf Eugen Fick and German medical student F. E. Muller in 1887. Further advances came in 1950, when Oregon optometrist Dr. George Butterfield created a corneal lens designed such that the inner surface of the lens was complimentary to the eye's shape, rather than flat.

Contact lenses finally came into widespread use by consumers in the 1960s with the development of soft, water absorbing ("hydrogel") polymers for contact lenses. Other significant developments in the field followed, include the advent of oxygen permeable lenses in the late 1970s, the development of extended wear contact lenses (which became available to consumers in 1981), and the introduction in 1995 of daily disposable contact lenses. At present, it is estimated that 125 million people use contact lenses worldwide (about 2% of the world's population), which includes some 28 to 38 million users in the United States alone.

While contact lenses offer several clear advantages over prescription glasses and other corrective vision measures currently known to the art, multiple use contact lenses require a certain amount of maintenance in order to function optimally and to remain comfortable during use. In particular, such contact lenses require periodic treatment for the removal of protein deposits and debris from the surfaces of the lenses, and also typically require periodic disinfection of the lenses. In the absence of such maintenance, the user's experience with the lenses typically begins to degrade, both in terms of the quality of vision provided by the lenses and the degree of comfort associated with wearing them. Failure to sanitize the lenses periodically may also result in potentially serious infections of the eyes and surrounding tissues.

Various methods have been developed in the art for the periodic treatment and disinfection of contact lenses. One common approach requires the user to remove the lenses periodically and to treat them with enzyme tablets that are dissolved in a liquid medium. The enzyme tablets are designed to remove or dislodge protein deposits and debris from the surfaces of the lenses. The enzyme tablets are typically designed to be dissolved in a 2% hydrogen peroxide solution, which has the further benefit of disinfecting the lenses while they are being cleaned.

In another approach known to the art for treating contact lenses, the lenses are disposed in a liquid medium and are exposed to subsonic frequencies, which act to dislodge protein deposits and other debris from the surfaces of the lenses. The liquid medium is then disinfected through prolonged exposure (e.g., for 15 minutes or more) to UV radiation and heat, which thus disinfects the lenses indirectly. In this approach, the cleaning device is typically designed so that the contact lenses being treated will not be directly exposed to the UV light source, since prolonged, direct exposure of the lenses to the UV light source for the time required for disinfection can damage the lenses.

Regardless of the methodology employed to treat and disinfect multiple use contact lenses, the cost and inconvenience of these procedures to the end user is significant. It is thus desirable to minimize the frequency of these treatments to the extent possible.

At present, the frequency of such treatments is often prescribed by the contact lens manufacturer, and may be based on statistical averages which may be derived, for example, from clinical studies or laboratory tests. For some users, the frequency of such treatments may be too great, and may thus represent an unnecessary cost and inconvenience. For other users, the frequency of these treatments may actually be too small. For still other users, the optimal frequency of treatment may change over time, and may depend on such factors as environmental conditions, physiological factors, health, and other such considerations.

A further problem facing wearers of contact lenses concerns damage to the lenses. As with any other article of manufacture, a certain percentage of contact lenses sold to consumers contain manufacturing defects. Such defects can adversely affect the ability of the lenses to function correctly or to sit properly upon the eye of the user, and may also cause discomfort to the user. Such defects may include scratches, tears, holes, peripheral damage, and wrinkles or bumps in the material of the lens, and may also include the presence of soil, debris or other foreign matter on the surfaces of the lens.

These defects may also result from handling of the lenses by the user. For example, some extended wear contact lenses require the user to clean the lenses daily or between uses. In many cases, this requires the user to manually apply a cleaning solution to the lenses. Although lenses for which this type of treatment is prescribed are typically designed to be sufficiently durable to withstand such treatment, they may be damaged by the process nonetheless. Such damage may result from unapparent weaknesses in the lens material, from failure by the user to follow proper procedures, or from the presence of contaminants on the lenses or on the user's hands at the time of cleaning.

This type of problem has existed in the art for some time, and various attempts have been made to address it. For example, U.S. Pat. No. 4,545,479 (Figari) and U.S. Pat. No. 4,784,258 (Figari) propose a contact lens carrying case which is equipped with a magnifying lens assembly and a light source, and which is designed to allow the user to visibly inspect lenses disposed within the carrying case for defects. U.S. Pat. No. 4,623,249 (Grant), U.S. Pat. No. 5,099,987 (Bieri), U.S. Pat. No. 5,337,888 (Morrison), and U.S. Pat. No. 6,092,646 (Glazier) disclose other contact lens carrying cases that also allow the user to inspect lenses disposed within the case. U.S. Pat. No. 5,440,458 (Volk) is also of interest in that it discloses an illuminated lens case for containing a plurality of lenses used in diagnostic procedures in darkened rooms, although the reference does not mention the use of the case disclosed therein in conjunction with contact lenses. U.S. Pat. No. 6,134,342 (Doke et al.) and U.S. Pat. No. 6,259,518 (Russell et al.) describe methods for examining lenses for defects at the manufacturing level.

While the foregoing devices and processes may be suitable for some purposes, in practice, these devices do not provide a clear indication of many of the types of defects that may be present in contact lenses, nor do these devices provide a satisfactory means for clearly viewing many of the types of deposits or debris that may be present on the surfaces of the lenses. There is thus a need in the art for a device that enables consumers to visually inspect the surfaces of contact lenses for the presence of defects, deposits or impurities. In particular, there is a need in the art for such a device that enables consumers to easily and conveniently gauge whether the lenses require cleaning, or need to be disposed of. There is further a need in the art for such a device which may be used to tailor cleaning of the lenses to such times when cleaning is actually required. These and other needs are met by the devices and methodologies disclosed herein and hereinafter described.

DETAILED DESCRIPTION

Figure 1:
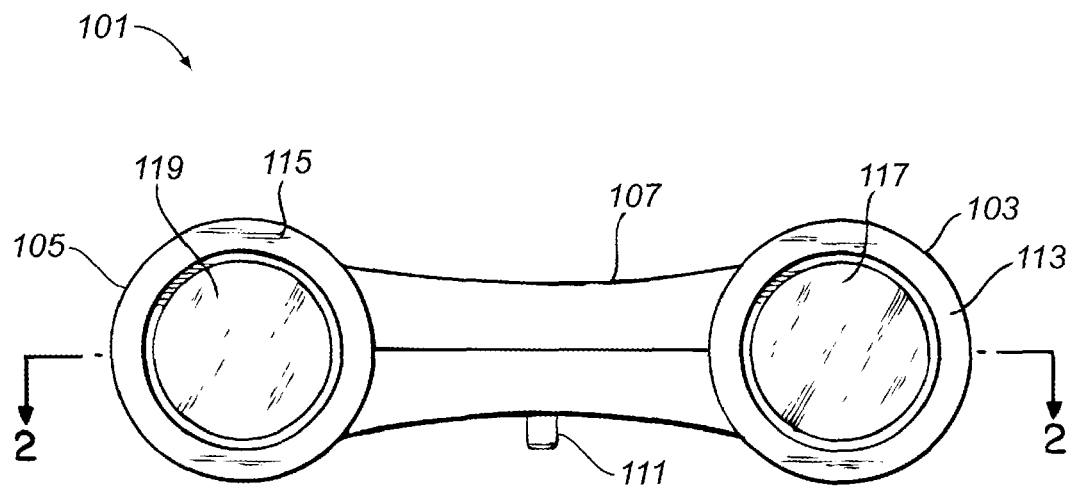
FIG. 1 is a top view of an embodiment of a contact lens case in accordance with the teachings herein.

It has now been found that the above noted needs may be met through the provision of a container or case for contact lenses which is equipped with an ultraviolet (UV) light source. The UV light source clearly illuminates deposits (such as proteins and lipids) that have formed on the lenses, thus making them readily visible to the user through one or more viewing windows provided in the walls or caps of the container. Indeed, many of the lipids and proteins that form on ophthalmic lenses are found to undergo fluorescence or phosphorescence upon exposure to UV light sources, thereby further improving their visibility on the lens surface. Consequently, the user can readily gauge whether the lenses require cleaning, or need to be disposed of. The UV light source also effectively illuminates any defects on the surface of the lenses, such as cracks or bumps, which may detract from their efficacy or from the comfort of the user when the lenses are being worn.

While other light sources, such as fluorescent light sources or tungsten filament light sources, may permit the detection of some impurities, deposits or defects on the surface of a contact lens, they do so very inefficiently. This is due, in part, to the poor contrast such light sources provide between the feature to be detected and the surrounding lens material. The use of a UV light source greatly improves this contrast, especially in the case of contact lenses which are provided with coatings or fillers designed to absorb UV radiation. Such coatings or fillers, which are often incorporated into contact lenses to protect the wearer's eyes from harmful radiation, cause the lenses to appear dark under a UV light source, thereby further highlighting the presence of any impurities on the surface of the lens that either do not absorb UV radiation as effectively, or that undergo fluorescence or phosphorescence upon exposure to a UV light source.

In many cases, the UV light source also more efficiently highlights defects in the lenses as compared to other light sources, since such defects typically interact differently with the UV light source than the remaining portion of the lens, and hence give rise to visible artifacts. For example, in many cases, a tear in the lens may disrupt the continuity of the UV absorbing coating or filler, and thus may appear as a jagged line, especially if the materials used in the construction of the lens holder interact with UV radiation differently than the lens itself. This may be the case, for example, if the contact lens holder is constructed from a pigment that fluoresces white at UV wavelengths.

As a further benefit, in many cases, the construction of the lens may cause it to act as a light pipe upon exposure to a source of UV or visible radiation. In such a case, the body of the lens may appear dark, but the edges of the lens may be brightly illuminated. Hence, any defects in the edges of the lenses are readily discernible. This phenomenon is especially useful in that the edges of contact lenses are a particularly common location for defects. In some cases, this effect may be magnified through the use of light pipes, lenses, prisms, prismatic films, or other means to focus or direct UV or visible radiation along the periphery of the lens.

Figure 2:
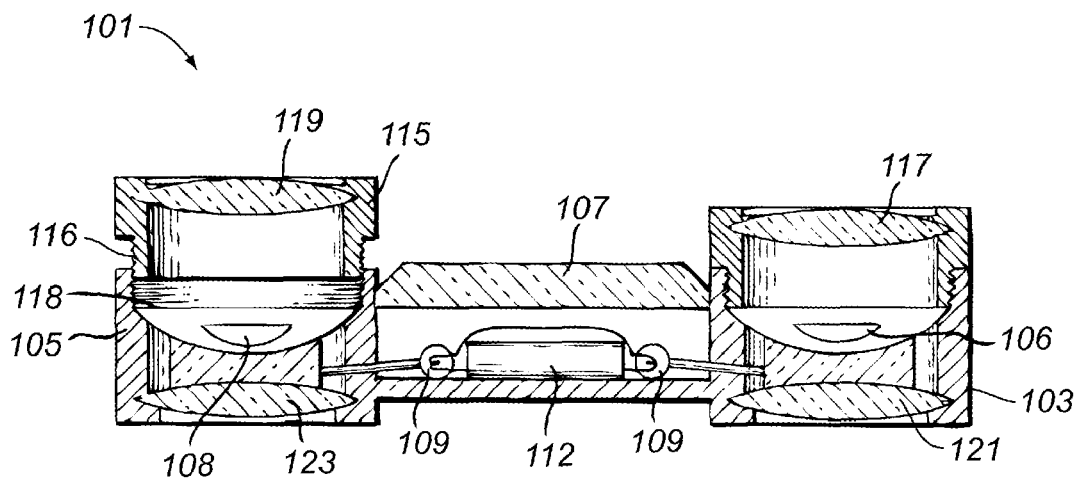
FIG. 2 is a cross-sectional view taken along LINE 2-2 of FIG. 1.
Figure 3:
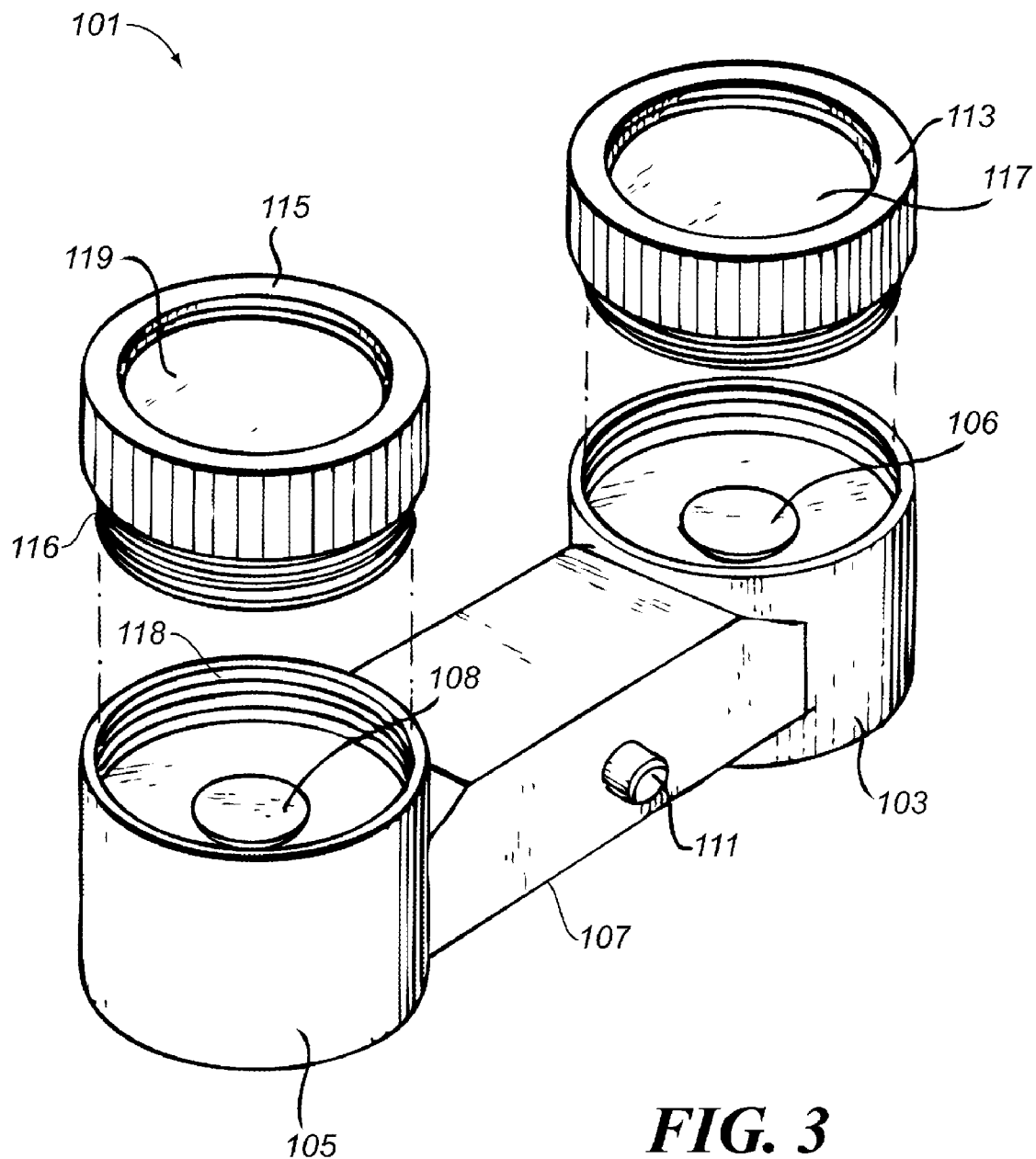
FIG. 3 is a perspective view of the contact lens case of FIG. 1.

FIGS. 1-3 depict a first particular, non-limiting embodiment of a container for ophthalmic lenses in accordance with the teachings herein. The container 101 depicted therein comprises a right chamber 103 and a left chamber 105 for accommodating lenses 106 and 108 designed for the user's right and left eyes, respectively. Chambers 103 and 105 are cylindrical in shape and are connected by means of a central section 107. The central section 107 houses a UV light source 109, preferably in the form of a UV bulb or LED, along with any necessary circuitry for operation of the UV light source 109.

In the particular embodiment depicted, the central section 107 is equipped with a dedicated UV light source 109 for each of the right 103 and left 105 chambers. However, it will be appreciated that, in other embodiments, a single UV light source may be utilized to illuminate both chambers. The UV light source 109 may be used in conjunction with various light cavities, optical fibers, light pipes, or light conduits, filters, louvers, and UV reflective or directing films or coatings to appropriately modify and direct the UV light emitted by the UV light source 109. For example, the device may be equipped with light conduits adapted to direct the light from the UV light source along the periphery of the lenses. Similarly, either or both of the chambers 103 and 105 may be coated or compounded with suitable materials to absorb, reflect, or direct UV radiation emitted by the UV light source 109.

Preferably, the central section 107 also includes a button-activated switch which can be toggled between an open state and a closed state by means of a button 111 mounted on the central section 107, thereby turning UV light source 109 on and off. The central section 107 is also preferably equipped with a power source 112 which, in this particular embodiment, is a small battery. This power source may be rechargeable, in which case the central section 107 may be equipped with a port or other suitable means (not shown) for electrically coupling it with a battery charger. The power source is preferably accessible through a removable panel (not shown) provided in the central section 107, thereby facilitating replacement of the power source as necessary.

Chambers 103 and 105 are equipped with caps 113 and 115, respectively. Caps 113 and 115 are provided with helical threads 116 that rotatingly engage complimentary shaped helical grooves 118 provided along the interior surface of each of chambers 103 and 105, thereby imparting a water-tight seal to these chambers. In this particular embodiment, caps 113 and 115 are equipped with first viewing windows 117 and 119, respectively, which enable the user to visually inspect one surface of lenses disposed within cylindrical housing members 103 and 105. As seen in FIG. 2, chambers 103 and 105 are also preferably equipped with second viewing windows 121 and 123, respectively, which enable the user to visually inspect the opposing surface of lenses disposed within cylindrical housing members 103 and 105.

Viewing windows 117, 119, 121 and 123 may comprise various transparent materials. These include, without limitation, various types of organic and inorganic materials, including quartz, various glasses, and various transparent polymeric films and materials, including various combinations of the foregoing. In some embodiments, one or more (and preferably all) of viewing windows 117, 119, 121 and 123 may comprise one or more lenses designed to magnify the contents of chambers 103 and 105.

Since UV radiation is harmful to the eyes, viewing windows 117, 119, 121 and 123 are preferably designed to be suitably transparent over at least a portion of the visible region of the spectrum so as to permit inspection of the lenses, but are preferably designed to be suitably opaque over at least a portion of the UV region of the spectrum so as to absorb or reflect UV radiation emitted by the UV light source. Preferably, viewing windows 117, 119, 121 and 123 are designed to be transparent over most of the visible region of the spectrum, but are designed to be opaque over most or all of the UV region of the spectrum, or at least over that portion of the UV spectrum coinciding with the UV footprint of the UV light source. This may be accomplished through the use of materials in viewing windows 117, 119, 121 and 123 that inherently possess these properties, or by treating, coating, or compounding the material of viewing windows 117, 119, 121 and 123 with materials that are suitably reflective or absorbing in the UV region of the spectrum.

Some specific, non-limiting examples of UV absorbing materials that may be used in the construction of viewing windows 117, 119, 121 and 123 include, but are not limited to, salicylates, cyanoacrylates, malonates, oxanilides, benzophenones, s-tiazines, azo dyes, and benzotriazoles.

Suitable azo dyes that are useful for this purpose include those formed by coupling a diazonium salt with another organic molecule which preferably contains an aromatic moiety. Some specific, non-limiting examples of the diazonium salt include those represented by Formulas I and II below:

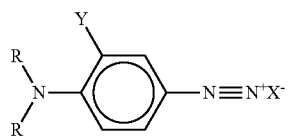

FORMULA I

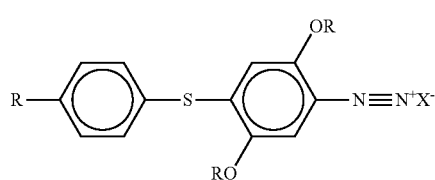

FORMULA II

In Formulas I and II, R may be hydrogen or an alkyl group, and is preferably methyl, ethyl, or propyl; Y is a halogen, and is preferably chlorine or fluorine; and X may be any suitable anion, but is preferably halogen, $NO_3^-$, $HSO_4^-$, $BE_4^-$, or $PF_6^-$.

The coupler molecule which reacts with the diazonium salt to form the diazo dye is preferably an aromatic molecule. Some specific, non-limiting examples of such coupler molecules are represented by Formulas III and IV below:

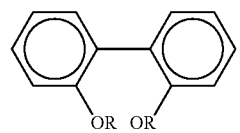

FORMULA III

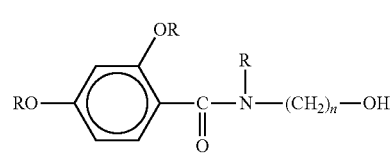

FORMULA IV

In the foregoing, R is hydrogen or alkyl as above, and for these particular couplers R is most preferably hydrogen or a low molecular weight alkyl; n is 0 or a whole number, and is most preferably 1, 2 or 3.

Suitable benzotriazoles for use in the construction of viewing windows 117, 119, 121 and 123 include, but are not limited to, those represented in FORMULAS V-VII below:

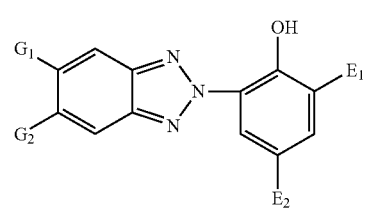

FORMULA V

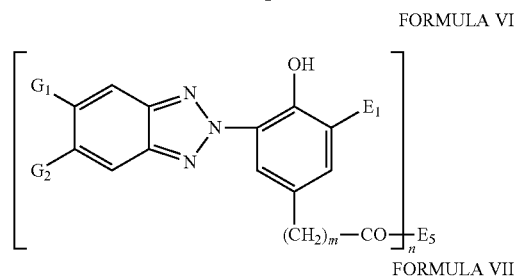

FORMULA VI

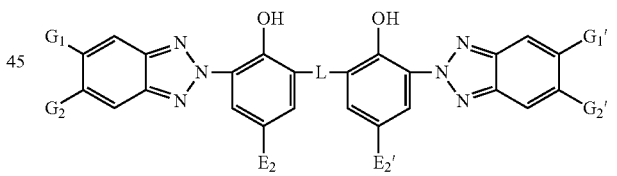

FORMULA VII

In FORMULAS V-VII, $G_1$, $G_1'$, $G_2$ and $G_2'$ are independently hydrogen, halogen, nitro, cyano, or perfluoroalkyl moieties;

$E_1$, $E_2$ and $E_2'$ are independently hydrogen or substituted or unsubstituted moieties selected from the group consisting of alkyl groups, alkenyl groups, cycloalkyl groups, phenyl groups, or phenylalkyl groups;

$E_5$ is $-PO(OE_{12})_2$, $-OSi(E_{11})_3$ or $-OCO-E_{11}$, or a straight or branched chain alkyl group which is interrupted by $-O-$, $-S-$ or $-NE_{11}$ and which can be unsubstituted or substituted by $-OH$ or $-OCO-E_{11}$; cycloalkyl which is unsubstituted or substituted by $-OH$; straight chain or branched alkenyl which is unsubstituted or substituted by $-OH$; aralkyl; $-CH_2-CHOH-E_{13}$; or glycidyl; and $E_{11}$, $E_{12}$ and $E_{13}$ are hydrogen, straight or branched alkyl groups, cycloalkyl groups, straight or branched alkenyl groups, aryl groups, or alkyl aryl groups.

One skilled in the art will appreciate that the specific choice of UV absorber may depend on a variety of factors. These include, for example, the spectral footprint of the UV light source and the material used to fabricate viewing windows 117, 119, 121 and 123.

Other suitable materials for use in viewing windows 117, 119, 121 and 123 include polymer films that are coated with single or multiple metal layers, and hybrid structures which may include both dyed films and metalized films. Still other suitable materials include Fabry-Perot interference structures. Examples of such structures are described, for example, in U.S. Pat. No. 6,650,478 (De Busk et al.).

Still other suitable materials for use in viewing windows 117, 119, 121 and 123 include UV absorbing glasses prepared by mixing ultrafine colloidal cerium oxide with glass-forming substances during the fabrication of the glass. Such glasses may be formed, for example, by admixing an aqueous colloidal dispersion containing 1-20 weight percent of 10-20 nm cerium oxide particles (optionally including a binder) with silica sand, after which the sand is dried, melted and cooled to give a relatively clear UV absorbing glass containing 0.3-2 weight percent cerium oxide.

Various UV light sources may be used in conjunction with the devices and methodologies disclosed herein. Preferably, these UV light sources are fluorescent light sources which utilize a single phosphor type and in which the bulb is housed within a glass envelop comprising a nickel-oxide/cobalt-oxide doped glass (Wood's glass) which blocks most visible light above 400 nanometers. In some embodiments, incandescent or mercury vapor light sources may also be used in combination with Wood's glass as the UV radiation source. In other embodiments, one or more UV LEDs may be utilized as the UV light source.

The particular choice of phosphor depends in part on the desired emission peak. Thus, europium-doped strontium fluorborate ($SrB_4O_7F:Eu^{2+}$) or europium-doped strontium borate ($SrB_4O_7:Eu^{2+}$) may be utilized to produce a near 368 to 371 nanometer emission peak, while lead-doped barium silicate ($BaSi_2O_5:Pb^+$) phosphors may be utilized to produce an emission peak around 350 to 353 nanometers.

In some embodiments of the devices described herein, the UV light source may be adapted not only to illuminate the surface of the lens, but also to disinfect the lens or the fluid medium in which the lens is stored. In such an embodiment, the case may be further equipped with a vibration source, such as a source of subsonic waves, which serves to dislodge contaminants from the surface of a lens. The contaminants may then be sterilized or mitigated with the UV radiation source.

In other embodiments of the devices described herein, it may be desirable to avoid direct, prolonged exposure of the lens to UV radiation for the durations typically required for sterilization, since doing so may damage the polymeric structure of the lens. In these embodiments, the case may be equipped with a first control that permits temporary and direct exposure of the lens to UV radiation for sanitation or disinfection purposes, and a second control which permits more prolonged exposure of the fluid medium (preferably with only indirect exposure of the lens) to the UV radiation source.

In further embodiments of the devices described herein, the device may include one or more sensors that detect one or more characteristics of one or more light beams (preferably comprising UV wavelengths) directed through a contact lens disposed within the device. The measured characteristics may be compared to a suitable reference signal to determine the presence of deposits, impurities or defects on the surfaces of the lens. For example, the wavelengths of the one or more light beams may be chosen to coincide with one or more absorption peaks of common proteins or lipids that deposit on contact lenses. The device may also be equipped with appropriate circuitry or other means for quantifying these values, and may be further equipped with a suitable display to convey this information to the user. In this type of embodiment, some or all of the viewing windows may be omitted.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A container for ophthalmic lenses, comprising:
   a chamber adapted to store an ophthalmic lens in a fluid medium; wherein said container comprises first and second chambers adapted to store first and second ophthalmic lenses in said fluid medium;
   a window for viewing a lens disposed in the chamber;
   a UV light source adapted to illuminate the lens with UV radiation; and wherein said first and second chambers are connected to a central portion which houses the UV light source.

2. The container of claim 1, wherein said first and second chambers are cylindrical.

3. The container of claim 1, wherein said first and second chambers are equipped with first and second removable caps.

4. The container of claim 3, wherein said first and second caps are equipped with first and second windows, respectively, that permit a lens disposed in the first and second chambers to be viewed.

5. The container of claim 4, wherein each of said first and second windows comprise a UV-absorbing material.

6. The container of claim 5, wherein the UV absorbing material is selected from the group consisting of salicylates, cyanoacrylates, malonates, oxanilides, benzophenones, s-tiazines, azo dyes and benzotriazoles.

7. The container of claim 6, wherein the UV absorbing material is an azo dye.

8. The container of claim 5, wherein the UV absorbing material is cerium oxide.

9. The container of claim 4, wherein each of said first and second windows comprise a UV reflecting material.

10. The container of claim 9, wherein the interior surface of each of said first and second chambers is equipped with a UV-absorbing material.

11. The container of claim 4, wherein each of said first and second windows comprise a UV-absorbing material.

12. The container of claim 4, wherein said first and second windows comprise a UV-absorbing material.

13. The container of claim 4, wherein said first and second windows comprise a UV-absorbing material.

14. The container of claim 4, wherein the first and second windows are essentially transparent to visible light.

15. The container of claim 1, wherein said first and second caps threadingly engage first and second helical threads disposed at one end of each of said first and second chambers.

16. The container of claim 1, wherein said UV light source is in optical communication with the interiors of said first and second chambers.

* * * * *